(12) United States Patent
Roy et al.

(10) Patent No.: US 7,628,781 B2
(45) Date of Patent: Dec. 8, 2009

(54) MEDICAL USAGE CONNECTOR ASSEMBLY FOR THE TRANSFER OF FLUIDS

(75) Inventors: Pierre Roy, Paris (FR); Alain Kleinsinger, Neuilly-sur-Seine (FR)

(73) Assignee: Eyegate Pharma S.A.S., Paris (FR)

( * ) Notice: Subject to any disclaimer, the term of this patent is extended or adjusted under 35 U.S.C. 154(b) by 0 days.

(21) Appl. No.: 10/507,057

(22) PCT Filed: Mar. 7, 2003

(86) PCT No.: PCT/FR03/00736

§ 371 (c)(1),
(2), (4) Date: Sep. 7, 2004

(87) PCT Pub. No.: WO03/076001

PCT Pub. Date: Sep. 18, 2003

(65) Prior Publication Data

US 2006/0025751 A1   Feb. 2, 2006

(30) Foreign Application Priority Data

Mar. 8, 2002   (FR) .................................. 02 02948

(51) Int. Cl.
*A61M 25/00* (2006.01)
(52) U.S. Cl. .................................................... 604/523
(58) Field of Classification Search ................. 604/905, 604/523, 256, 533, 149.1, 408, 535, 534, 604/536, 537, 411–414
See application file for complete search history.

(56) References Cited

U.S. PATENT DOCUMENTS 2,922,419 A   1/1960   Bednarz
3,491,757 A   1/1970   Arce
4,161,949 A * 7/1979   Thanawalla .................. 604/411
4,214,586 A * 7/1980   Mericle ....................... 606/154
5,221,267 A * 6/1993   Folden ......................... 604/200
5,810,398 A * 9/1998   Matkovich ...................... 285/3
5,820,614 A * 10/1998  Erskine et al. ............... 604/533
5,868,433 A * 2/1999   Matkovich ...................... 285/3
6,423,053 B1 * 7/2002  Lee ............................. 604/533
6,595,981 B2 * 7/2003  Huet ........................... 604/523

FOREIGN PATENT DOCUMENTS

DE           19614684 A        12/1996
WO           WO 9944652         9/1999

* cited by examiner

*Primary Examiner*—Nicholas D Lucchesi
*Assistant Examiner*—Christopher D Koharski
(74) *Attorney, Agent, or Firm*—Foley & Lardner LLP; Michel Morency; James F. Ewing

(57) ABSTRACT

The invention relates to a connector assembly (10) for the transfer of fluids, particularly fluids comprising an active agent from a reservoir to a medical device for dosage, comprising: a first connector element (20), pertaining to the reservoir with first fixing means (23), a second connector element (10), pertaining to the medical dosage device with second fixing means (12), cooperating with the first fixing means to give an irreversible connection between the two elements. The first and second elements are embodied such as to cooperate with other by clipping on a single translational movement of a connector element relative to the other to produce the irreversible connection, characterized in that at least one of the connection elements is embodied with means to render the same breakable.

27 Claims, 4 Drawing Sheets

FIG_1a

FIG_1b

FIG_1c

FIG_2a

FIG_2b

FIG_2c

FIG_3

FIG_4

FIG_5

MEDICAL USAGE CONNECTOR ASSEMBLY FOR THE TRANSFER OF FLUIDS

CROSS REFERENCE TO RELATED APPLICATIONS

The present application is a non-provisional application of International Application No. FR 2003/000736, filed Mar. 7, 2003.

FIELD OF THE INVENTION

The invention relates to a connection system for medical use adapted to transfer of fluids, particularly medicines, from a reservoir to a medical delivery device.

BACKGROUND OF THE INVENTION

Since risks of cross contaminations between different patients or between patients and care givers have been taken into consideration, it is now customary or even compulsory for the medical delivery device to be used once only for a specific patient, as certified by the development of "disposable" equipment sold as being sterile and discarded after use. Similarly, medicines are more and more frequently sold in vials containing a single dose, making it impossible to use it on several patients and limiting risks of dosage errors. However, despite the "disposable" indication signalled by medical delivery devices, there is nothing to prevent them from actually being reused on several patients. Thus for example, a needle for an intravenous injection can be connected to a syringe containing a dose of medicine and can therefore be used to deliver the said dose to several patients. Many solutions have been proposed firstly to the problem of reuse of these hypodermic needles and syringes, and secondly to accidental contamination by the injection, and invariably lead to single use of the syringe and/or the needle.

However, some medicines are in a form that needs to be prepared by dilution, for example a freeze-dried powder. Preparation of such a medicine consists of mixing the form to be diluted with a solvent in specific proportions and transferring the solution obtained into the medical delivery device. In general, the solvent is drawn up firstly with the syringe and is then injected into the receptacle containing the freeze-dried powder. After mixing, the mix is drawn up with the syringe again. The syringe is then connected to the medical delivery device so that the said mix can be administered. Consequently, the connection between the syringe and the various receptacles must be made and disassembled as often as necessary, in order to make the mix. The last connection made is the connection between the syringe and the medical delivery device.

U.S. Pat. No. 6,231,552 describes a connection assembly between a reservoir, in this case a syringe, and a medical delivery device, in this case a hypodermic needle. At the syringe, this connection assembly uses a standard male Luer cone surrounded by a coaxial cylinder at the cone with a thread on the internal face, and a notch is formed at the free end of the thread. The needle has a standard female Luer cone compatible with the male Luer cone on the syringe and a thread complementary to the thread on the syringe formed on the outer surface of the base of the hypodermic needle. Furthermore, a pin projects from the said external surface at the distal end of the needle thread. Thus, when the syringe is connected to the needle, after screwing to make the two threads mentioned above cooperate, the pin on the hypodermic needle clips irreversibly into the notch in the syringe provided for it. The resulting system prevents the reservoir and the medical delivery device from being disconnected, while enabling the standard male and female "lock" type Luer connectors to be reversibly connected (with a thread like that described above). The system becomes irreversible only when making the connection between Luer cones including either the projecting pin or the notch in which the pin will fit.

The disadvantage of this type of device is that the user must make a translation movement combined with a rotation movement (helical movement) to irreversibly connect such a system, and to make the connection while providing an additional force of the end of screwing to engage the said irreversible retaining means between the two elements, while the male and female Luer cones are already cooperating by contact so as to make the connection leak tight.

SUMMARY OF THE INVENTION

One purpose of the invention is to provide an irreversible connection assembly between a reservoir and a medical delivery device assembled during an extremely single connection movement.

To achieve this purpose according to the invention, a connection assembly is provided for transfer of fluid, particularly fluid containing active products, from a reservoir to a medical delivery device comprising a first connection element associated with the reservoir and comprising first retaining means, a second connection element associated with the medical delivery device and comprising second retaining means capable of cooperating with the first retaining means to form an irreversible connection between the two connection elements, the first and second retaining means being arranged such that they cooperate with each other by clipping during a simple translation movement of one connection element with respect to the other to make the connection irreversible.

Thus, this particular arrangement of retaining means enables the user connecting a medical delivery device to a reservoir, both being equipped with such connection elements, to irreversibly connect them to each other by making a single translation movement, as he would normally do with standard connection elements such as male and female Luer cones.

Advantageously, all connection elements have at least one of the following additional characteristics:

- either the first or second retaining means comprises at least one elastically deformable tab and the other retaining means comprises at least one lip capable of cooperating with the said tab,
- either the first or second retaining means comprises two tabs located on opposite sides of the connection element,
- either the first or second retaining means comprises at least one recess and the other retaining means comprises at least one lip capable of cooperating with the recess,
- the lip is elastically deformable,
- either the first or second connection element comprises a male part and the other connection element comprises a female part with a shape complementary to the male part and capable of cooperating with the male part so as to make the connection leak tight,
- the male and female parts are Luer cones with a taper of about 6%,
- the male part is an essentially tubular shaped perforator, and
- at least one of the connection elements comprises means capable of making it breakable.

The invention also includes a connection element for the transfer of fluid, particularly a fluid containing active products, from a reservoir to a medical delivery device containing retaining means arranged so as to cooperate with the retaining means in another connection element by clipping during a translation movement between the two connection elements so as to make an irreversible connection between the two connection elements.

BRIEF DESCRIPTION OF THE DRAWINGS

Other characteristics and advantages of the invention will become clearer after reading the following description of one embodiment and variants. In the attached drawings.

DETAILED DESCRIPTION

In this document, "fluid" refers to various medicines or active products obtained by chemical synthesis or a natural extract compound, designed to care or treat an infection or a body injury, or to correct or modify an organic function, or to produce a diagnostic. For example, anti-inflammatory drugs, antibiotics, antiviral agents, fungicides, anticancer agents, antiangiogenic agents, antiglaucomatous agents, neuroprotectors, neuromodulators, anesthetics, products intended for genic therapy such as oligonucleotides, plasmids, and nutrients, vitamins, salts, minerals and hormone products. A fluid may also be a body fluid such as blood or one of its compounds, gastric juices, urine, etc.

For further information about the definition of a medicine, the European Directive 65/65/CEE, Jan. 26 1965 dealing with legal requirements related to medicines gives the following definition:

"The following definitions are applicable in application of this directive:

1. Pharmaceutical specialty: any medicine prepared in advance, marketed under a special name and within special packaging.

2. Medicine: Any substance or composition presented as having remedial or preventive properties with regard to human or animal diseases.

Any substance or composition that can be administered to man or animal in order to produce a medical diagnostic or to restore, correct or modify organic functions in man or animal is also considered as being a medicine.

3. Substance: Any material regardless of its origin, which may be:

human such as human blood and products derived from human blood, animal such as micro-organisms, whole animals, parts of organs, animal secretions, toxins, substances obtained by extraction, products derived from blood, etc.

vegetable such as micro-organisms, plants, parts of plants, vegetable secretions, substances obtained by extraction, etc.

chemical such as elements, natural chemical materials and chemical transformation and synthesis products.

4. Magistral formula: any medicine prepared in a pharmacy using a prescription intended for a specific patient.

5. Officinal formula: any medicine prepared in a pharmacy according to the indications in a pharmacopoeia and that will be issued directly to patients supplied through this pharmacy".

This is completed by Directive 2309/93, Jul. 22 1993:

"Medicines derived from one of the following biotechnological processes:

recombining deoxyribonucleic acid technology, controlled expression of coding genes for proteins biologically active in prokaryotes and eukaryotes, including transformed mammal cells, methods based on hybridomes and monoclonal antibodies.

Veterinary medicines, including medicines not derived from biotechnology, intended for use mainly as performance enhancers to promote growth or to increase the productivity of treated animals".

The following definitions are applicable in the remainder of the document:

Medical delivery device, a device designed to come into contact with a tissue of the human body (skin, mucous membrane, muscle, etc.), or to penetrate into one of the cavities of the human body (oral or nasal cavity, bladder, genitals, eye, lung, etc.) or to penetrate into a circulation system (vein, artery) so as to enable systemic or local administration of a therapeutic active product or to sample a body fluid, in other words a fluid like that defined above. Examples include the following devices considered as being a medical delivery device: transdermic patch, intramuscular vaccination system, transdermic vaccination system, intravenous catheter, urethral probe, gastric probe, hypodermic needle, system for delivery of medicines by iontophoresis, by electroporation or other energy source, bronchial sampling catheter, etc.

Medicine or fluid reservoir. A reservoir containing the medicine ready to be administered. It may be a flexible or rigid single dose vial, a vial containing a treatment designed to be administered over several days either continuously (for example a flexible perfusion pack), or discontinuously (for example antibiotic treatment), a syringe containing the medicine dose after preparation, an aerosol vial, etc. This medicines reservoir is always provided with an end piece enabling a connection with the medical device, for example such as a standard Luer cone for a syringe or a perforatable rubber stopper for a rigid glass vial, Luer, a standard male or female connection element composed of a cone with a taper of about 6%, and an inlet diameter of about 4 mm (for the male) and about 4.30 mm (for the female), used for medical purposes, defined by ISO international standards and used on all perfusion and transfusion lines (intravenous catheter, syringe and hypodermic needle, etc.), Spike, a hollow metal or plastic needle used to perforate rubber stoppers (septa) for medicine containers (vials) to access the contents. There is no particular standard for these spikes, only on vials.

Figure 1A:
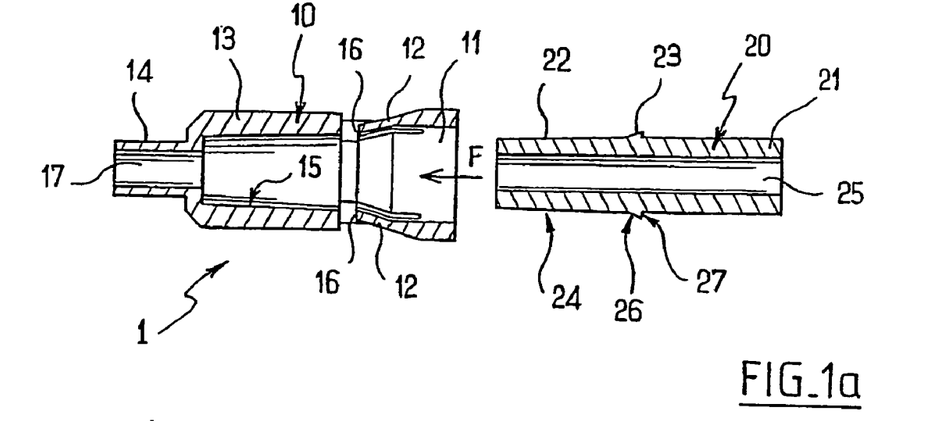
FIGS. 1a, 1b and 1c are sectional and three-dimensional views of a first embodiment of the invention in the disconnected position and then in the connected position.
Figure 1B:
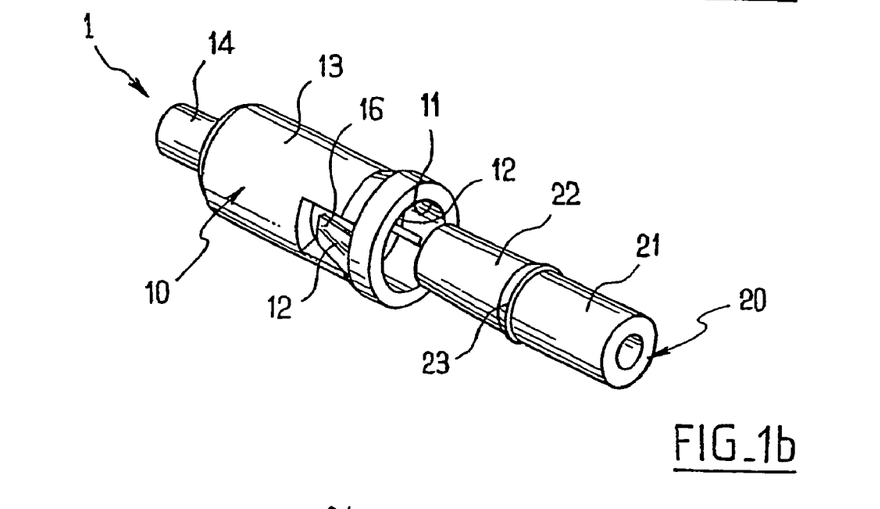
Figure 1C:
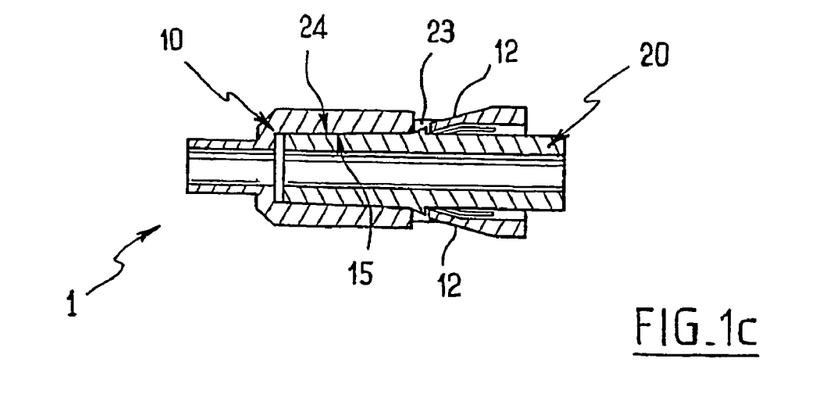

We will describe a first embodiment of the invention with reference to FIGS. 1a to 1c. The connection assembly 1 comprises two connection elements 10, 20 capable of cooperating with each other so as to make a connection that is firstly irreversible and secondly leak tight.

The connection element 10, also called the female connector, is generally in an elongated shape of revolution. An internal duct 17 passes through it, from one side to the other and coaxial with the axis of revolution (not shown). The female connector 10 comprises three functional parts. The first part 14 is preferably an interface area with the medical delivery device. This part enables an attachment of the female connector onto the medical delivery device (not shown). For example, in the case illustrated in FIG. 1, this area is essentially tubular shaped and is capable of receiving a needle or a tube that is preferably assembled by gluing or insert moulding. This entire interface area 14 may be a part of the medical delivery device. In this case, the female connector 10 forms part of the medical delivery device and is integrated into it.

The second functional part of the female connector is a leak tight area 13 with a generally tubular external shape and with an internal face 15 in this case with a contact approximately equivalent to a female Luer cone as defined above and delimiting a part of the internal duct 17.

The third part of the female connector is an area 11 designed to cooperate with the other connection element to make an irreversible connection.

The area 11 of the female connector 10 comprises a ring and a series of tabs 12 derived from the material used for the ring. These tabs have a free end 16 extending into the internal duct 17 and along the direction in which the male connector 20 is inserted into the female connector 10 illustrated by the arrow F. These tabs 12 are elastically deformable.

The connection element 20, or the male connector, is generally in an elongated shape of revolution. An internal duct 25 passes through it, from one side to the other and coaxial with the axis of revolution (not shown). Similarly, the male connector 20 comprises three functional parts as follows. The part 21 is an interface area with the reservoir containing the medicine. In the same manner as above, this interface area 21 preferably forms part of the medicines reservoir. In this case, it is in the form of any essentially tubular area. Preferably, this entire interface area 21 may be a part of a medicines reservoir. Thus, the male connector 20 forms a part of the reservoir and consequently is integrated into it. For example, as we will be seen later, a single dose flexible medicine vial could be fitted with such a male connector.

A second part 23 is designed to cooperate with the area 11 of the female connector so as to make the connection irreversible. The part 23 comprises a lip 23 projecting from the external surface of the male connector. The lip 23 is preferably continuous around the entire circumference of the male connector 20, as illustrated in FIG. 1b. The lip 23 has a first face 26 inclined at an angle preferably between approximately 10° and 45° with the axis of revolution of the male connector, then a second face 27 approximately perpendicular to the axis of revolution. The intersection of the faces 26, 27 forms a vertex of the lip 23. The face 26 is along the direction of introduction illustrated by arrow F, and face 27 is on the opposite side.

Finally, the third part forming the male connector is a leak tight area 22 with an external surface 24 approximately equivalent to a male Luer cone as described above.

The female connector 10 is assembled with the male connector 20 using a single translation movement along the direction of the arrow F. When the male connector is inserted into the female connector, the lip 23 will deform the tabs 12 elastically, the face 26 pushing their end 16 back, and then once the vertex of the lip 23 has passed, the ends 16 in the tabs 12 return to their initial position then preventing disconnection of the two connection elements. If an attempt is made to perform a reverse translation movement along the direction of the arrow F, the ends 16 of the tabs 12 stop in contact with the lip 23, particularly in contact with face 27, thus preventing the movement. Once the male connector 20 has been inserted into the female connector 10, the leak tight area 22 cooperates with the leak tight area 13 through a contact between the female Luer cone 15 and the male Luer cone 24, thus making the said connection leak tight due to their complementary shape. Thus, the fluid passing through the internal duct 25 of the male connector can then circulate in the internal duct 17 in the female connector towards the medical delivery device without any loss of fluid towards the outside at the connection assembly. The assembly made is illustrated in FIG. 1c.

Note that the part 22 forming the leak tight area of the male connector 20 is approximately equivalent to a female Luer cone that connects the medicines reservoir to any other device comprising a standard Luer type female connector. This makes it possible to make solutions from freeze dried products and solvents that require a connection with the device containing the solvent and then a connection with the device containing the freeze dried product so as to make the solution before connecting to the medical delivery device.

Figure 2A:
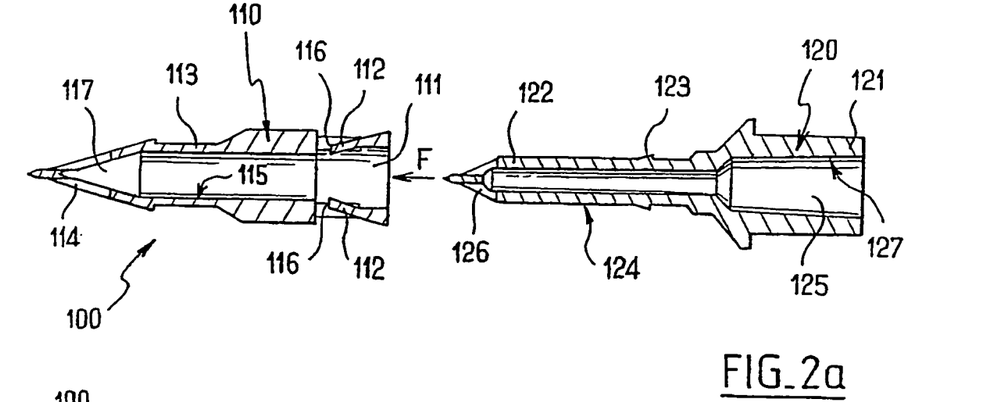
FIGS. 2a, 2b and 2c are sectional and three-dimensional views of a variant of the embodiment in FIG. 1.
Figure 2B:
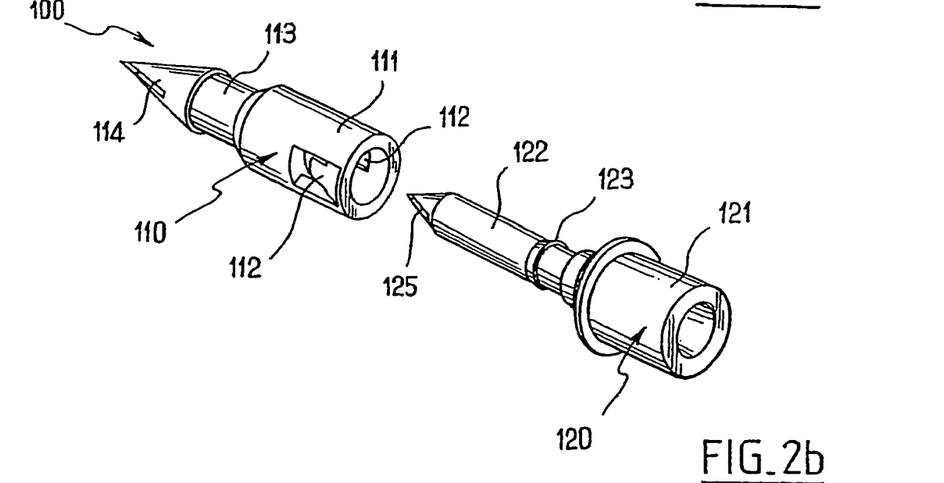
Figure 2C:
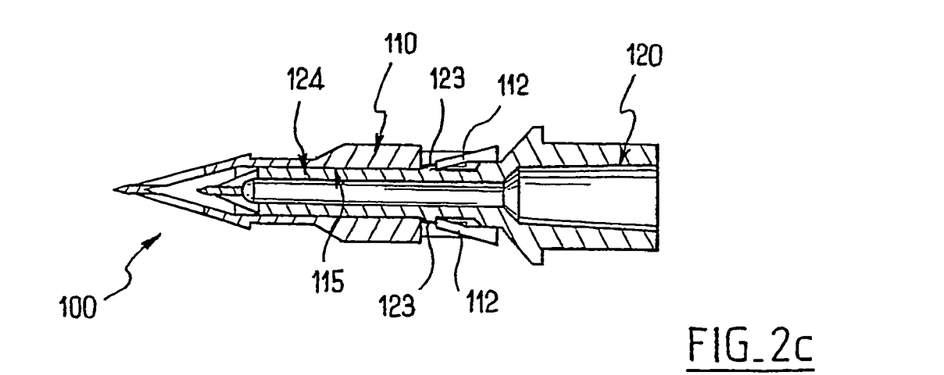

We will now describe a variant of the previous embodiment, with reference to FIGS. 2a to 2c. The connection assembly 100 comprises a connection element 10 or female connector and a connection element 120 or male connector. In the same way as above, each of the connectors is in an elongated shape of revolution. It comprises an internal duct 117, 125 coaxial with the axis of revolution (not shown). It has three functional parts. The female connector 110 has a functional part 114 that will make the interface with the medicine device presented here in the form of a conical beam forming an end piece that will be force fitted into a flexible tube connected to the medical delivery device. Preferably, as in the previous case, the entire interface area 114 forms part of the medical delivery device and thus the medical connector 110 forms an integral part of the medical delivery device. The female connector 110 has a second part 113 that forms the leak tight area with an essentially tubular internal contact face 115 and that is capable of cooperating with the complementary shape of the male connector 120 as we will describe below. Finally, the female connector 110 has a third part 111 very similar to the part 11 of the previous embodiment comprising a ring 111 and two tabs 112 opposite each other on each side of the internal duct 117. As described above, the tabs are made from the same material as the ring of the connector 110, and have a free end 116 facing the direction of insertion illustrated by the arrow F, and also facing the inside of the duct 117.

The male connector 120 is provided with an internal duct 125 used to transfer fluid from a medicines reservoir not shown, to an opposite end 126. This male connector 120 has three functional parts. The part 121 is designed to make the interface with a medicines reservoir. This interface is made in exactly the same way as in the previous embodiment. It is possible that this interface comprises a female Luer type cone 127 designed to cooperate with a standard syringe with a complementary male Luer cone forming the reservoir. The male connector 120 then has a part forming a leak tight area 122 comprising an essentially tubular external surface 124 capable of cooperating with the surface 115 of the female connector 110 so as to make the connection leak tight. Finally, the male connector 120 has an area 123 that cooperates with the lip 123 projecting outwards, designed to cooperate with the tabs 112 of the female connector 110 to make the connection irreversible. The assembly illustrated in FIG. 2c is manufactured and assembled in the same way as the assembly in the previous embodiment illustrated in FIG. 1c and described above.

Note that in FIGS. 2a to 2c, the area 122 of the male connector 120 is advantageously in the form of a spike capable of perforating rubber stoppers of medicine vials. For example, it would be possible to imagine that this type of connector could be installed or could form an integral part of a syringe for sampling sterile water, or any other solvent for injection, contained in a vial with a stopper. This sterile water could then be transferred into a second vial with a stopper containing freeze dried active products in order to dilute the freeze dried active products and obtain a solution, and then making an irreversible permanent connection with a medical delivery device comprising a female connector 110 described above.

Figure 3:
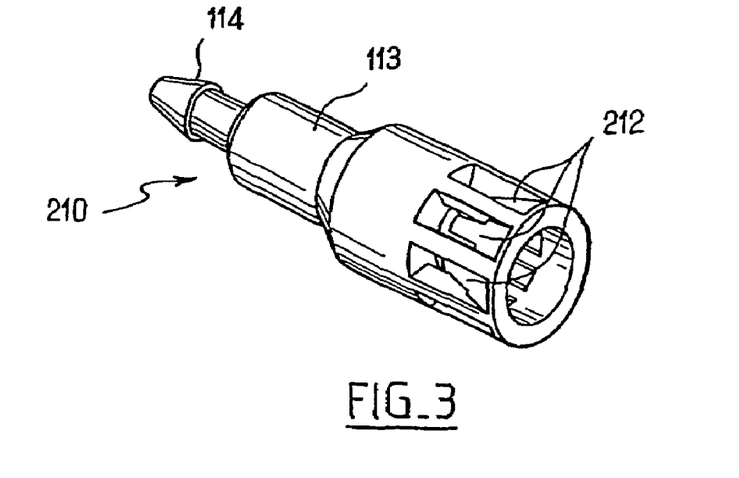
FIG. 3 is a three-dimensional view of a second variant embodiment of a connection element in FIG. 1.

The minimum number of tabs 12 or 112 is 1. However, it is very advantageous to have an even number of tabs uniformly distributed around the ring of the female connector. One variant embodiment is illustrated in FIG. 3 in which the female connector 210 is different from the female connector 110 in that it comprises 8 tabs 212 uniformly distributed around the ring of the connector 210. Industrially, the use of two tabs as illustrated in FIGS. 1a to 2c is preferable, since it facilitates the manufacture of the female connector by plastic injection.

Figure 4:
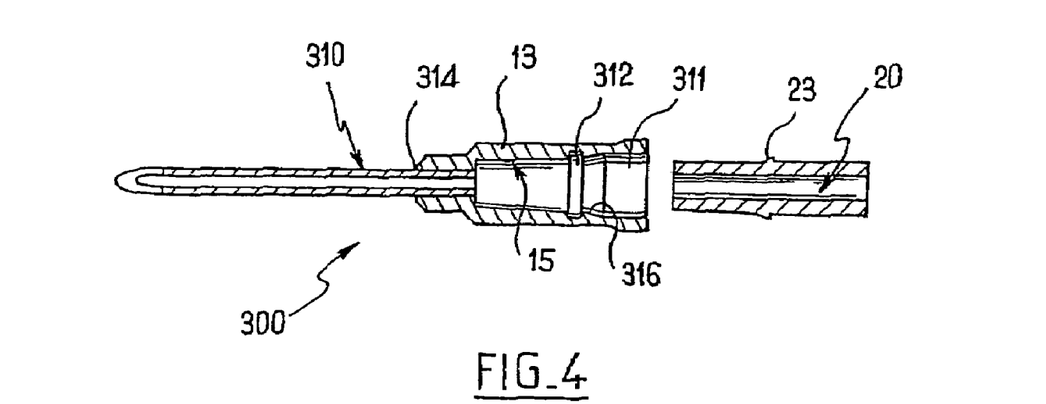
FIG. 4 is a sectional view of a third variant embodiment of the connection assembly in FIG. 1.

A second variant embodiment of a female connector is illustrated in FIG. 4, and consists of making a continuous recess in the form of a ring 312. In this case, the connection assembly 300 comprises a male connector 10 like that described above and a female connector 310 associated with a needle 314 and with a structure identical to the connector 10 described above. This connector 310 is also differentiated from the connector 10 by the fact that the area 311 does not have any tabs, but instead it has a recess in the form of a ring 312 in which the lip 23 of the male connector 20 will fit during assembly. This type of embodiment requires that the material from which the connector 310 is made should be an elastic material allowing deformation of a cone 316 located between the recess and the connector entry, through the lip 23 so as to allow the lip 23 to pass through until it reaches the recess 312.

Figure 9:
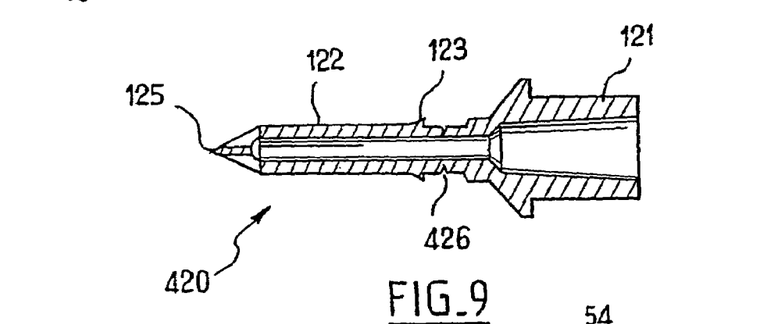
FIG. 9 is a sectional view of a second embodiment of the invention.
Figure 10:
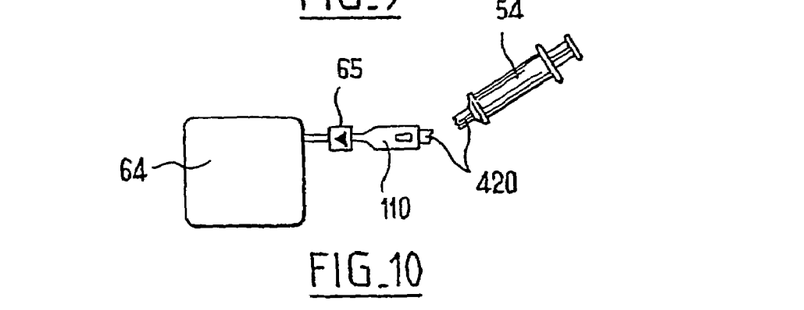
FIG. 10 illustrates a method of using the invention in FIG. 9.

We will now describe a variant embodiment of the male connector 120, with reference to FIGS. 9 and 10. The male connector 420 is identical to the male connector 120 except that it is provided with a continuous notch 426 around its entire outer periphery between the lip 123 and the part 121 forming the interface area with the medicines reservoir. This notch 426 weakens the male connector 420 at this location, such that the connector will break at this location if a small shear force is applied. This so-called breakable area means that once the fluid has been transferred between the medicines reservoir and the medical delivery device, the said reservoir can be broken off from the said device leaving a part of the male connector in the female connector. This means that the medicines reservoir part can be separated from the delivery medical device once the medicine has been transferred, to avoid uselessly increasing the size of the said medical delivery device during use. Moreover, the fact that part of the male connector is left in the female connector makes it even more difficult to use the female connector, and therefore the medical delivery device, afterwards. This situation is illustrated in FIG. 10 in which a female connector 110 is connected to a medical delivery device 64 through a non-return valve 65, or an non-reflux valve, that prevents fluid from coming out after injection and rupture of the male connector. In this case, the male connector 420 is shown broken off at the notch 426 and forms an integral part of a syringe forming a medicines reservoir 54.

Note that preferably, in general, the male connector described forming the connection assembly is fully integrated into the medicines reservoir, and the complementary female connector is fully integrated into the medical delivery device.

Figure 5:
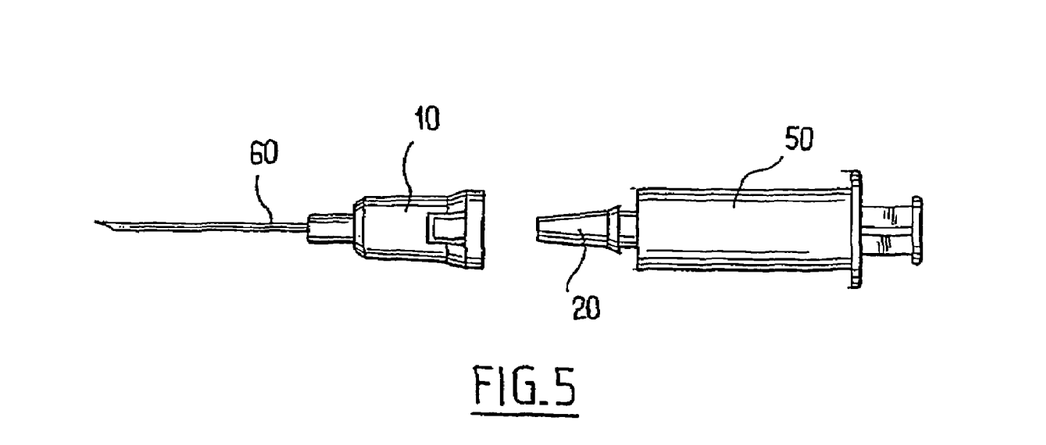
FIG. 5 illustrates the first method of using the invention in FIG. 1.

FIG. 5 illustrates a first method of using a connection assembly illustrated in FIGS. 1a to 1c, in this case the female connector 10 is installed fixed to a hypodermic needle 60 that could also be a catheter or a probe. The male connector is also installed in a fixed manner on a single dose or multi-dose syringe containing the medicine. It is important to note that in this type of configuration, the syringe may be connected reversibly with a standard female Luer. For example, it is consequently possible to sample a medicine or a body fluid from a source equipped with a standard female Luer connector, to disconnect from it after the medicine or the fluid has been sampled, and then to inject this fluid into the needle or the catheter mentioned above without necessarily disconnecting the medical delivery device 60 again.

Figure 6:
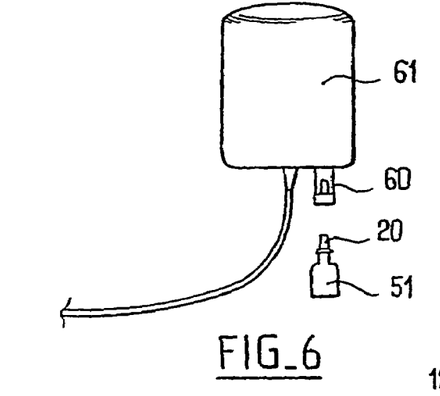
FIG. 6 illustrates a second method of using the invention in FIG. 1.

FIG. 6 illustrates a second method of using the connection assembly shown in FIGS. 1a to 1c, in which the medical delivery device is a perfusion pack prefilled with a solute (for example glucosed water) and having a female connector 10 integrated into it to mix the solute of the pack 61 with a single medicine dose, for example such as an antibiotic. A single-dose vial 51 forming a medicines reservoir and integrating a male connector 20 may be installed irreversibly into the female connector 10. The fact that this type of connector is placed on the access path to the perfusion pack then makes it impossible to reuse this access, and is a simple means of preventing any risk of accidental overdose of the medicine to be injected.

Figure 7:
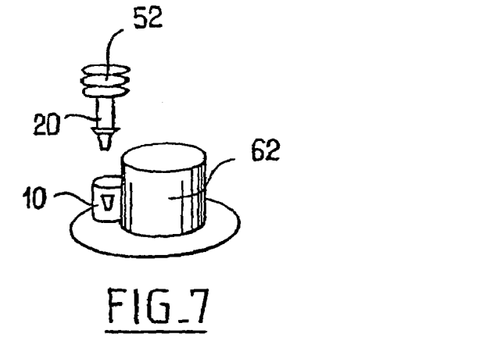
FIG. 7 is a third method of using the invention in FIG. 1.

FIG. 7 illustrates a third method of using the connection assembly in FIG. 1a to 1c. In this example, the medical delivery device is a device for transfer of intraocular or transdermic or transmucous medicine, in which the female connector 10 forms an integral part of the device. An intraocular medicine transfer device is described in more detail in French patent application FR 2 773 320. Consequently, a flexible single-dose vial 52 is equipped with a connector 20. With this single-dose vial, the assembly is unusable a second time after it has been connected to the medical delivery device and after the medicine has been transferred from the vial to the medical delivery device.

Figure 8:
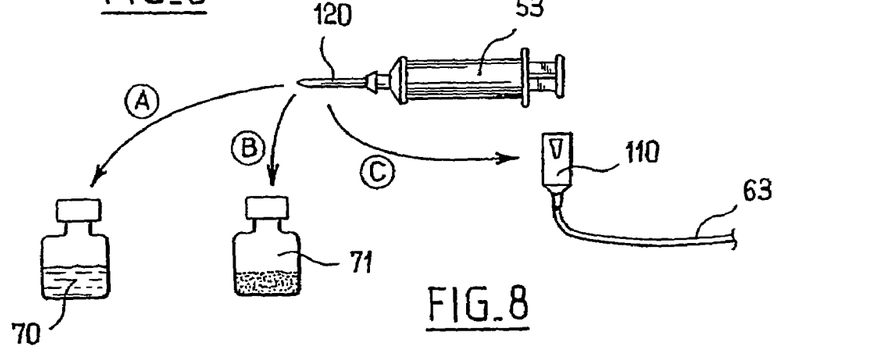
FIG. 8 illustrates a method of using the invention in FIG. 2 for freeze-dried products.

FIG. 8 illustrates a method of using the invention as illustrated in FIGS. 2a to 2c.

This figure illustrates a procedure to be followed for preparation of a medicine in freeze-dried form. The male connector in the form of a spike 120 is installed fixed onto the syringe or any other medicines reservoir provided with a suction device. In the first step A, the necessary quantity of solution is drawn up by perforating the septum of the vial 70 containing it. In step B, the previously drawn in solution is injected into a vial 71 containing a freeze-dried product by perforating the septum of the vial 71 in the same manner. The solution is then drawn back into this vial. In step C, the syringe 53 is irreversibly connected into a female connector 110 connected to the medical delivery device 63 illustrated in the figure simply by a supply cable.

The materials used to make this type of connector are preferably polymer materials frequently used for manufacturing connectors for devices for medical purposes, naturally having elastic properties enabling clipping by deformation of connector tabs while providing good mechanical strength and being suitable for injection moulding or moulding in a shaped mould. For example, materials in the polystyrene, polycarbonate, polyvinyl chloride, polyethylene, polypropylene, polyurethane, polyamide, polysulfone families, etc. can be used, without this list being exhaustive. Moreover, some metallic alloys may be suitable for this application, the aptitude for reversible elastic deformation being a criterion for the choice of such alloys.

Note also that the female connector in the preferred embodiments illustrated in the figures cannot be used with standard male Luer connectors.

Obviously, many modifications could be made to the invention without departing from its scope.

For example, the male connector may have deformable tabs with a deformable free end on the outside facing the direction of insertion, instead of a lip 23. The female connector may have a lip instead of the tabs 12, projecting towards the inside of the duct 17 and capable of cooperating with the tabs on the male connector to make the connection irreversible, and during insertion the lip deforms the tabs that return to their initial positions after insertion. Any reverse movement to disconnect the assembly is made impossible due to the fact that the said tabs stop in contact with the lip.

The invention claimed is:

1. A connection assembly for transferring a fluid, particularly a fluid containing active products, from a reservoir to a medical delivery device comprising:
    a first connection element associated with the reservoir and comprising first retaining means and a reservoir interface;
    a second connection element associated with the medical delivery device and comprising a medical delivery interface and second retaining means capable of cooperating with the first retaining means to form an irreversible connection between the two elements;
    wherein the first and second connection elements further comprise a perforator capable of piercing a medicine vial, which is reversibly connectable to standard connectors allowing fluid transfer therethrough before an irreversible connection is made with the other element, the respective retaining means is positioned between the perforator and the respective interface; and
    wherein the first and second retaining means are arranged such that they cooperate with each other by clipping during a single translation movement of one connection element with respect to the other to make the connection irreversible; and
    wherein each perforator is aligned in the same direction at the time of the irreversible connection.

2. The connection assembly according to claim 1, wherein either the first or second retaining means comprises at least one elastically deformable tab and the other retaining means comprises at least one lip capable of cooperating with the tab.

3. The connection assembly according to claim 2, wherein either the first or second retaining means comprises two tabs located on opposite sides of the first or second connection element.

4. The connection assembly according to claim 1, wherein either the first or second retaining means comprises at least one recess and the other retaining means comprises at least one lip capable of cooperating with the recess.

5. The connection assembly according to claim 2, wherein the lip is elastically deformable.

6. The connection assembly according to claim 1, wherein either the first or second connection element comprises a male part and the other connection element comprises a female part with a shape complementary to the male part and capable of cooperating with the male part so as to make the connection leak tight.

7. The connection assembly according to claim 6, wherein the male and female parts are Luer cones with a taper of about 6%.

8. The connection assembly according to claim 6, wherein the male part is an essentially tubular shaped perforator.

9. The connection assembly according to claim 1 wherein the assembly also comprises non-return means capable of preventing fluid from coming out after injection.

10. The connection assembly according to claim 1, wherein a weakened area in at least one of the first and second connection elements renders the at least one connection element breakable at the weakened area in response to a shear force applied thereto.

11. The connection assembly according to claim 8, wherein the second connection element makes use of the perforator to make reversible to make reversible connections onto receptacles before an irreversible connection is made with the first connection element.

12. A connection element for transfer of fluid, particularly fluid containing active products, from a reservoir to a medical delivery device, comprising:
    a first retaining means associated with a first interface, wherein the first retaining means are arranged such that they cooperate with a second retaining means in another connection element by clipping during a single translation movement between the two connection elements to make an irreversible connection between the two connection elements, the second retaining means associated with a second interface; and
    wherein the first and second retaining means further comprises a perforator capable of piercing a medicine vial, which is reversibly connectable to standard connectors allowing fluid transfer therethrough before an irreversible connection is made with the other element, the respective retaining means is positioned between the perforator and the respective interface; and
    wherein each perforator is aligned in the same direction at the time of the irreversible connection.

13. The connection assembly according to claim 10, wherein the weakened area comprises a notch.

14. The connection assembly according to claim 13, wherein the notch is continuous around an outer periphery of the at least one connection element.

15. The connection assembly according to claim 3, wherein the lip is elastically deformable.

16. The connection assembly according to claim 4, wherein the lip is elastically deformable.

17. The connection assembly according to claim 4, wherein the assembly also comprises non-return means capable of preventing fluid from coming out after injection.

18. A method for forming a connection for transferring a fluid, particularly a fluid containing active products, between a reservoir and a medical delivery device comprising the steps of:
    (i) reversibly connecting at least one of a first connection element having a perforator capable of piercing a medicine vial, the first connection element associated with the reservoir and a second connection element having a perforator capable of piercing a medicine vial, the second connection element associated with the medical delivery device to respective standard connectors via the perforator allowing fluid transfer therethrough before an irreversible connection is made with the other connecting element;

(ii) translating the first connection element having a first retaining means and a reservoir interface relative to the second connection element having a second retaining means and a medical delivery device interface, the respective retaining means is positioned between the perforator and the respective interface;

(iii) irreversibly connecting together the translated first and second connection elements through cooperation of the first and second retaining means, wherein each perforator is aligned in the same direction at the time of the irreversible connection; and (iv) transferring a fluid between the reservoir and the medical delivery device through the irreversibly connected first and second connection elements.

19. The method of claim 18, further comprising applying a shear force to at least one of the irreversibly connected first and second connection elements causing at least one of the first and second connection elements to break at a weakened area provided therein.

20. The method of claim 19, wherein the weakened area comprises a notch.

21. The method of claim 20, wherein the notch is continuous around an outer periphery of the at least one connection element.

22. The means of claim 12, wherein a weakened area in at least one of the first and second retaining means renders the at least one retaining means breakable at the weakened area in response to a shear force applied thereto.

23. The method of claim 19, wherein the at least one of the first and second connection elements broken by application of the shear force is unable to form another irreversible connection with another one of the first and second connection elements.

24. The connection assembly according to claim 1, wherein the perforator is in a form of a spike.

25. The connection assembly according to claim 2, wherein either the first or second connection element comprises a male part and the other connection element comprises a female part with a shape complementary to the male part and capable of cooperating with the male part so as to make the connection leak tight.

26. The connection assembly according to claim 3, wherein either the first or second connection element comprises a male part and the other connection element comprises a female part with a shape complementary to the male part and capable of cooperating with the male part so as to make the connection leak tight.

27. The connection assembly according to claim 4, wherein either the first or second connection element comprises a male part and the other connection element comprises a female part with a shape complementary to the male part and capable of cooperating with the male part so as to make the connection leak tight.

* * * * *